United States Patent [19]

Nelson

[11] Patent Number: 5,097,052
[45] Date of Patent: Mar. 17, 1992

[54] PREPARATION OF SODIUM ALUMINUM ALKYLS

[75] Inventor: Gunner E. Nelson, Baton Rouge, La.

[73] Assignee: Ethyl Corporation, Richmond, Va.

[21] Appl. No.: 695,446

[22] Filed: May 3, 1991

[51] Int. Cl.$^5$ ............................. C07F 5/06; C07F 1/04
[52] U.S. Cl. ..................................................... 556/190
[58] Field of Search ............... 556/190, 170, 188, 189; 260/660 R

[56] References Cited

U.S. PATENT DOCUMENTS 3,711,529  1/1973  Shepperd, Jr. .................. 556/190 X
4,060,540  11/1977  Bernady et al. ................ 556/190 X

*Primary Examiner*—Arthur C. Prescott
*Attorney, Agent, or Firm*—Terry B. Morris; Steven R. Eck

[57] ABSTRACT

Novel methods for the preparation of sodium aluminum tetraalkyls have been discovered comprising the reaction of sodium aluminum tri-isobutyl hydride and olefins. The methods avoid the use of sodium aluminum hydrides and permit in one step both the substitution of isobutyl groups and additions at hydride hydrogens to produce sodium aluminum tetraalkyls.

8 Claims, No Drawings

PREPARATION OF SODIUM ALUMINUM ALKYLS

BACKGROUND

Sodium aluminum tetraalkyls are useful compounds in the chemical industry. One particular use is their reaction with silane and halosilanes to produce alkylsilanes. For instance, see U.S. Pat. No. 4,670,574 and U.S. Pat. No. 4,711,965. Methods to produce sodium aluminum tetraalkyls can include the reaction of sodium aluminum hydride and olefins. Sodium aluminum hydride can require high pressures to produce, is expensive and can be i0 dangerous in handling, requiring expensive safeguards. Accordingly, methods of producing tetraalkylsilanes without the use of sodium aluminum tetraalkyls have been devised. For instance, in U.S. Pat. No. 4,595,777, trialkylaluminum and haloalkylsilanes are reacted to produce tetraalkylsilanes. In another instance, in U.S. Pat. No. 4,845,260 a three step method of reacting an alkali metal with aluminum, hydrogen and an olefin at elevated pressures in the presence of an organoaluminum catalyst (e.g. triethylaluminum) is first performed, followed by addition of more catalyst to the reaction mixture to form an intermediate mixture, which is then reacted with trihalosilane to produce a tetraalkylsilane.

Great Britain 763,824 discloses processes for the production of hydrocarbon substituted aluminum compounds in which a hydride of aluminum, or a derivative thereof in which one or more hydrogen atoms have been substituted by monovalent saturated hydrocarbon radicals, is heated with a hydrocarbon mono-olefin or poly-olefin at such a temperature that an addition product of the metallic starting compound and the olefin is formed and decomposition or other secondary changes of the starting materials and of the products do not take place to any substantial extent. An alternative presented in '824 is to first convert aluminum trialkyl into a complex alkali trialkyl aluminum hydride by addition of lithium hydride or sodium hydride with a subsequent reaction with an olefin to produce an alkali aluminum tetraalkyl.

Methods of producing sodium aluminum tetraalkyls without using sodium aluminum hydride remain of value.

SUMMARY

Novel methods for the preparation of sodium aluminum tetraalkyls have been discovered comprising the reaction of sodium aluminum tri-isobutyl hydride and olefins. The methods can be performed under relatively lower pressures, avoid the use of sodium aluminum hydride, and permit in one step both the substitution of isobutyl groups and additions at hydride hydrogens to produce sodium aluminum tetraalkyls.

DESCRIPTION OF PREFERRED EMBODIMENTS

In one embodiment the present invention is a method for producing a sodium aluminum tetraalkyl comprising reacting sodium aluminum tri-isobutyl hydride and an olefin to produce the sodium aluminum tetraalkyl. The embodied reaction is a one-step reaction whereby during the reacting the olefin performs a substitution reaction upon the isobutyl groups of the sodium aluminum triisobutyl hydride and also performs during the reaction an addition reaction upon the hydride hydrogen of the sodium aluminum tri-isobutyl hydride Such a reaction can be represented by the following equation:

$$NaAl(iso\text{-}butyl)_3H + 4R \rightarrow NaAlR'_4, \quad (I)$$

where "iso-butyl" represents an iso-butyl group, R represents an olefin and R' represents the reacted olefin as an alkylated group onto the aluminum atom. For instance, when R is 1-octene (i.e., $CH_2=CH-(CH_2)_5-CH_3$) the reaction is sodium aluminum tri-isobutyl hydride with 1-octene to form sodium aluminum tetraoctyl and can be represented by the following equation:

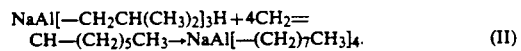

$$NaAl[-CH_2CH(CH_3)_2]_3H + 4CH_2= CH-(CH_2)_5CH_3 \rightarrow NaAl[-(CH_2)_7CH_3]_4. \quad (II)$$

The olefin used is preferably a straight-chain 1-alkene and can be represented by the formula:

$$CH_2=CH(CH_2)_nCH_3 \quad (III)$$

where n is an integer from 0 to about forty. Preferably the olefin is a straight-chain 1-alkene having from four to about twenty carbon atoms. Although not preferred, some attached alkyl groups can be present to make branched structures, such as 3-methyl-1-octene. Similarly, the olefin may contain aromatic or non-aromatic isocyclic hydrocarbon substituents.

The reaction can be performed in a pressure vessel. The preferred pressures of the reaction unexpectedly can range from about one atmosphere to about eleven atmospheres. The reaction autogeneously creates pressure by the formation of gaseous isobutylene. Unexpectedly, the reactions can be conducted with periodic venting-off of the formed isobutylene preferably such that near atmospheric conditions are maintained for a substantial portion of the reaction. The reaction temperature can range from about 100° C. to about the decomposition temperatures of the reactants under the conditions of pressures used. Preferably, the temperatures range from about 150° C. to about 300° C.

The embodied reaction can provide a convenient nonsodium aluminum hydride route to silahydrocarbons. An embodied preferred method of producing silahydrocarbon comprises the steps of:

(1) reacting sodium hydride and tri-isobutynol to produce sodium aluminum tri-isobutyl hydride, (2) reacting the produced sodium aluminum tri-isobutyl hydride and an excess of an olefin to produce a sodium aluminum tetraalkyl, and (3) reacting in proportions about three moles of the sodium aluminum tetraalkyl and about four moles of methyltrichlorosilane to produce about four moles of a methyltrialkylsilane and about three moles of sodium aluminum tetrachloride, wherein step (2) is conducted at a temperature of from about 150° C. to about 300° C., preferably about 170° C. to about 175° C., and wherein the excess of olefin ranges from about stoichiometric to about 6 moles of olefin per equivalent weight of sodium an wherein venting off of autogenous pressure is performed during step (2).

The olefin used in the reaction is as described hereinabove, preferably a straight-chain 1-alkene as represented in formula (III). The venting of pressure during step (2) is such that the pressure during reaction is maintained at from about one to eleven atmospheres, preferably with periodic or continuous venting off to maintain the pressure in the lower portion of pressure ranges, e.g. near atmosphere.

The following experiments illustrate embodiments of the present invention but are not intended to limit the scope of the invention herein.

EXPERIMENT 1

62.7 grams of tri-isobutylaluminum, which assayed at 13.7 weight percent (0.318 moles) aluminum, were mixed together with 7.15 grams of sodium hydride, which assayed at 97 weight percent (0.289 moles). The mixing was with stirring under a nitrogen atmosphere and was heated briefly at 125° C. The reaction mass thereby formed was allowed to cool. Upon cooling, a reaction product, sodium aluminum triisobutyl [NaAl(i-butyl)$_3$H], solidified from the reaction mass, which was an indication of completion of reaction.

The sodium aluminum triisobutylhydride was charged into a pressure vessel together with 2.54 moles (100 percent excess) of octene-1. Stirring of the material in the vessel was then performed while the material was heated to a temperature range of 170°-175° C. Periodically, the temperature was reduced by cooling to about 110° C. and isobutylene was vented from the vessel. This cycle of heating and cooling was repeated a total of three times.

Upon cooling after the final cycle, samples of the material were taken from the vessel for analysis. The analysis show that the reaction mass had 2.76 weight percent aluminum and 0.39 mmoles per gram of evolved gases. The analysis correspond empirically to a formula of NaAl(octyl)$_{3.62}$R$_{0.38}$, were R is isobutyl or hydrogen. A total of 289.1 grams of the aluminate was collected without correction for sampling losses, which corresponds to a value of 93 percent recovered aluminum.

0.295 moles of the aluminate were then charged into a pressure vessel together with 0.310 moles of methyltrichlorosilane. This mixture was stirred and heated to a temperature of 185°-190° C. for five hours. The reaction mass was then allowed to cool. Cooled reaction mass was then mixed with a 20 percent caustic solution to hydrolyze any residual aluminate. After separation of the organic phase, GLC analysis showed that 89.9 grams of methyltrioctylsilane had been produced, which corresponds to a theoretical yield of 76.2 percent. A small amount of residual material was also detected which was possibly methyldioctylsilane.

EXPERIMENT 2

134.3 grams of tri-n-octylaluminum, which assayed at 6.87 weight percent (0.338 moles) aluminum, and 0.317 moles of sodium hydride were mixed together and heated at 125°-130° C. for about two hours. After two hours, substantially all of the sodium hydride appeared to have been dissolved.

The liquid product was then mixed with 190 grams of octene-1 (5 times 0.338 moles) into a pressure vessel. This mixture was heated for one hour at 125° C. and then subsequently heated for three hours at 175° C. The heated product was allowed to cool. Analysis of the cooled product solution showed a content of 2.68 weight percent aluminum and 0.02 mmoles per gram of gas. This corresponded to an empirical formula of NaAl(octyl)$_{3.98}$H$_{0.02}$.

0.291 moles of the aluminate and 0.291 moles of methyltrichlorosilane were mixed and heated as in the previous example. The GLC analysis of the organic phase generated on hydrolysis of this mixture indicated that methyltrioctylsilane was produced with an 89.6 weight percent yield.

What is claimed is:

1. A method of producing a sodium aluminum tetraalkyl comprising reacting sodium aluminum tri-isobutyl hydride and an olefin to produce said sodium aluminum tetraalkyl whereby during said reacting said olefin performs a substitution reaction upon the isobutyl groups of said hydride and performs an addition reaction upon the hydride hydrogen of said hydride.

2. The method of claim 1 wherein said olefin is a straight-chain 1-alkene.

3. The method of claim 2 wherein said 1-alkene comprises from four to about twenty carbon atoms.

4. The method of claim 1 wherein the reactions are conducted at a pressure ranging from about one atmosphere to about eleven atmospheres.

5. The method of claim 4 wherein the reactions are conducted with venting of formed isobutylene.

6. The method of claim 5 wherein the venting is sufficient to maintain the pressure at about atmospheric pressure.

7. A method of producing a sodium aluminum tetraalkyl comprising the steps of:
   (1) reacting sodium hydride and tri-isobutyl aluminum to produce sodium aluminum tri-isobutyl hydride,
   (2) reacting the produced sodium aluminum triisobutyl hydride and an excess of an olefin to produce a sodium aluminum tetraalkyl, and
   (3) reacting in proportions about three moles of the sodium aluminum tetraalkyl and about four moles of methyltrichlorosilane to produce about four moles of a methyltrialkylsilane and about three moles of sodium aluminum tetrachloride, wherein step (2) is conducted at a temperature of from about 150° C. to about 300° C. and wherein the excess of olefin ranges from about stoichiometric to about 6 moles of olefin per equivalent weight of sodium and wherein venting off of autogenous pressure is performed during step (2).

8. The method of claim 7 wherein step (2) is conducted at a temperature of from about 170° C. to about 175° C.

* * * * *